United States Patent
Wierzbicki et al.

(10) Patent No.: US 6,593,312 B2
(45) Date of Patent: Jul. 15, 2003

(54) CYCLIC α-AMINO-γ-HYDROXYAMIDE COMPOUNDS

(75) Inventors: Michel Wierzbicki, L'Etang la Ville (FR); Jean-Marie Fourquez, Suresnes (FR); Nigel Levens, Vaucresson (FR); Bernadette Husson-Robert, Nanterre (FR); Olivier Nosjean, Rueil Malmaison (FR); Michelle Boulanger, Chatou (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 10/173,993

(22) Filed: Jun. 18, 2002

(65) Prior Publication Data

US 2003/0004138 A1 Jan. 2, 2003

(30) Foreign Application Priority Data

Jun. 18, 2001 (FR) .............................. 01 07934

(51) Int. Cl.$^7$ .................. A61K 31/425; A61P 3/10; C07D 277/04
(52) U.S. Cl. .................. 514/76; 514/423; 514/620; 514/623; 514/365; 548/200; 548/540; 558/170; 564/164; 564/188; 564/189
(58) Field of Search .............. 548/200, 540; 514/365, 423, 76, 620, 623; 558/170; 564/164, 188, 189

(56) References Cited

PUBLICATIONS

Clausen, et al 2002, J. Nat. Prod., 65 542–547.*
Katagiri, et al, 1994, 59, 8101–8106.*

\* cited by examiner

Primary Examiner—Joseph K. McKane
Assistant Examiner—Andrea D. Small
(74) Attorney, Agent, or Firm—The Firm of Hueschen and Sage

(57) ABSTRACT

A compound of formula (I):

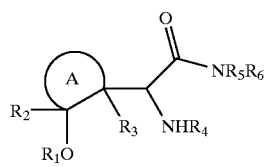

wherein:

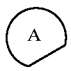

represents an optionally substituted saturated carbon ring having from 4 to 8 ring members, $R_1$ and $R_4$, which may be identical or different, each represents hydrogen or acyl, $R_2$ and $R_3$, which may be identical or different, each represents hydrogen or alkyl, $R_5$ and $R_6$, which may be identical or different, each represents hydrogen or alkyl, or $R_5$ and $R_6$ together, with the nitrogen atom carrying them, form an optionally substituted nitrogen-containing heterocycle, stereoisomers thereof, and also addition salts thereof with a pharmaceutically acceptable acid.

Medicinal products containing the same which are useful for treatment of glucose intolerance or of disorders associated with hyperglycaemia.

14 Claims, No Drawings

CYCLIC α-AMINO-γ-HYDROXYAMIDE COMPOUNDS

DESCRIPTION OF THE PRIOR ART

A cyclic α-amino-γ-hydroxy acid compound has been described in the journal J. Org. Chem. 1994, 59 (26), 8101–6, without their having been any pharmacological activity mentioned for that compound.

BACKGROUND OF THE INVENTION

In addition to the fact that they are new, the compounds of the present invention have valuable pharmacological properties. They have blood glucose-lowering properties, rendering them beneficial in the treatment of glucose intolerance and disorders associated with hyperglycaemia, such as type II diabetes or obesity.

DETAILED DESCRIPTION OF THE INVENTION

The present invention relates more specifically to compounds of formula (I):

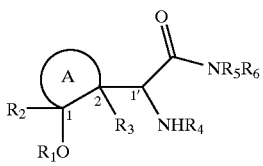

(I)

wherein:

represents a saturated carbon ring having from 4 to 8 ring members, optionally substituted by one or more linear or branched ($C_1$–$C_6$)alkyl groups, $R_1$ and $R_4$, which may be identical or different, each represents a hydrogen atom or a linear or branched ($C_1$–$C_6$)acyl group, $R_2$ and $R_3$, which may be identical or different, each represents a hydrogen atom or a linear or branched ($C_1$–$C_6$)alkyl group, $R_5$ and $R_6$, which may be identical or different, each represents a hydrogen atom or a linear or branched ($C_1$–$C_6$)alkyl group, or $R_5$ and $R_6$ together, with the nitrogen atom carrying them, form a nitrogen-containing heterocycle optionally substituted by one or more identical or different groups selected from the groups cyano, $CO_2R_7$ (wherein $R_7$ represents a hydrogen atom or a linear or branched ($C_1$–$C_6$)alkyl group), $COR_7$ (wherein $R_7$ is as defined hereinbefore), nitro, $CONR_{8a}R_{8b}$ (wherein $R_{8a}$ and $R_{8b}$, which may be identical or different, each represents a hydrogen atom or a linear or branched ($C_1$–$C_6$)alkyl group or $R_{8a}$ and $R_{8b}$ together form a nitrogen-containing heterocycle), $S(O)_nR_9$ (wherein n represents 1, 2 or 3, and $R_9$ represents a hydrogen atom, a linear or branched ($C_1$–$C_6$)-alkyl group or an aryl group) and $PO_3R_{10a}R_{10b}$ (wherein $R_{10a}$ and $R_{10b}$, which may be identical or different, each represents a hydrogen atom or a linear or branched ($C_1$–$C_6$)-alkyl group), to stereoisomers thereof, and also to addition salts thereof with a pharmaceutically acceptable acid.

Amongst the pharmaceutically acceptable acids there may be mentioned, without implying any limitation, hydrochloric, hydrobromic, sulphuric, phosphoric, acetic, trifluoroacetic, lactic, pyruvic, malonic, succinic, glutaric, fumaric, tartaric, maleic, citric, ascorbic, oxalic, methanesulphonic, benzenesulphonic, camphoric acid, etc.

A nitrogen-containing heterocycle is to be understood as an optionally bridged, saturated mono- or bi-cyclic group having from 5 to 12 ring members and containing one, two or three hetero atoms, one of those hetero atoms being the nitrogen atom and the additional hetero atom or atoms optionally present being selected from the atoms oxygen, nitrogen and sulphur. Preferred nitrogen-containing heterocycles are the groups pyrrolidinyl, thiazolidinyl, piperidyl, morpholinyl, azabicyclo[3.3.0]octyl and piperazinyl.

An aryl group is to be understood as phenyl, biphenylyl, naphthyl or tetrahydronaphthyl, each of those groups optionally being substituted by one or more identical or different atoms or groups selected from the halogen atoms and the groups linear or branched ($C_1$–$C_6$)alkyl, hydroxy, linear or branched ($C_1$–$C_6$)alkoxy, linear or branched ($C_1$–$C_6$)polyhaloalkyl, nitro and ($C_1$–$C_2$)alkylenedioxy.

Preferred compounds of formula (I) are those wherein

represents a carbon ring having 5 or 6 ring members.

An advantageous variant of the invention concerns compounds of formula (I) wherein $R_5$ and $R_6$ together form an optionally substituted nitrogen-containing heterocycle. Among those, preference is given especially to such compounds in which $R_5$ and $R_6$ together form an optionally substituted pyrrolidine or an optionally substituted thiazolidine.

Amongst the preferred compounds of the invention, the following may be mentioned more especially:

(1R,2S,1'S)-2-[1'-amino-2'-oxo-2'-(1-pyrrolidinyl)ethyl] cyclohexanol, its (1S,2R,1'R) enantiomer, and also addition salts thereof with a pharmaceutically acceptable acid;

(1R*,2R*,1'R*)-2-[1'-amino-2'-oxo-2'-(1-pyrrolidinyl) ethyl]cyclopentanol, and also addition salts thereof with a pharmaceutically acceptable acid, wherein a (1R*,2R*,1'R*) compound is to be understood as a racemic mixture of the 2 enantiomers having the absolute configurations (1R,2R,1'R) and (1S,2S,1'S);

(1R,2S,1'R)-2-[1'-amino-2'-oxo-2'-(1-pyrrolidinyl)ethyl] cyclopentanol, its (1S, 2R,1'S) enantiomer, and also addition salts therof with a pharmaceutically acceptable acid;

(1R,2S,1'S)-2-[1'-amino-2'-oxo-2'-(1-pyrrolidinyl)ethyl] cyclopentanol, its (1S, 2R,1'R) enantiomer, and also addition salts thereof with a pharmaceutically acceptable acid;

(1R,2S,1'R)-2-[1'-amino-2'-oxo-2'-(1-pyrrolidinyl)ethyl] cyclohexanol, its (1S,2R,1'S) enantiomer, and also addition salts thereof with a pharmaceutically acceptable acid;

and (1R,2S,1'R)-2-[1'-amino-2'-oxo-2'-(1,3-thiazolidin-3-yl)ethyl]cyclohexanol, its (1S,2R,1'S) enantiomer, and also addition salts thereof with a pharmaceutically acceptable acid.

The invention extends also to a process for the preparation of compounds of formula (I), which process is characterised in that chloroacetyl chloride is reacted with a compound of formula (II):

HNR₅R₆ (II)

wherein R₅ and R₆ are as defined for formula (I), to yield a compound of formula (III):

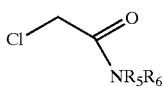
(III)

wherein R₅ and R₆ are as defined hereinbefore, which is converted into an amine of formula (IV):

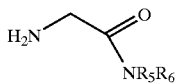
(IV)

wherein R₅ and R₆ are as defined hereinbefore, which is reacted with benzaldehyde to yield a compound of formula (V):

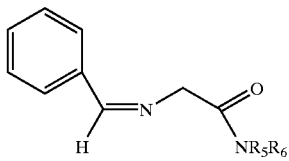
(V)

wherein R₅ and R₆ are as defined hereinbefore, which is reacted with a compound of formula (VI):

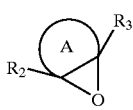
(VI)

wherein

,

R₂ and R₃ are as defined for formula (I), to yield, after optional acylation of the hydroxy function, a compound of formula (VII), which is of the relative configuration trans:

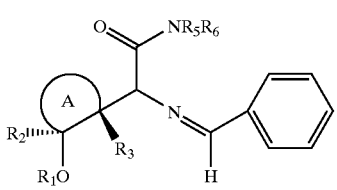
(VII)

wherein

,

R₁, R₂, R₃, R₅ and R₆ are as defined hereinbefore, which is converted by hydrolysis followed, if desired, by acylation of the amino function, to yield a compound of formula (Ia) of the relative configuration trans, a particular case of the compounds of formula (I):

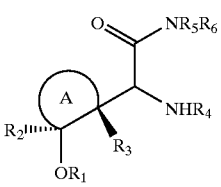
(Ia)

wherein

,

R₁, R₂, R₃, R₄, R₅ and R₆ are as defined hereinbefore, which is converted, if desired, into a compound of formula (Ib) of the relative configuration cis, a particular case of the compounds of formula (I):

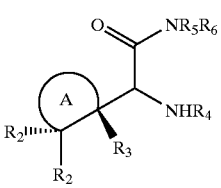
(Ib)

wherein

,

R₁, R₂, R₃, R₄, R₅ and R₆ are as defined hereinbefore, which compounds of formulae (Ia) and (Ib) are separated, if desired, into their isomers by conventional separation techniques, are purified, if necessary, by conventional methods of purification, and are converted, if desired, into addition salts with a pharmaceutically acceptable acid.

The compounds of formula (Ic), a particular case of the compounds of formula (I):

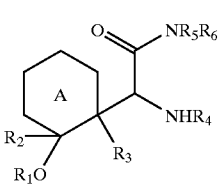
(Ic)

wherein

represents a saturated carbon ring having 6 ring members optionally substituted by one or more linear or branched ($C_1$–$C_6$)alkyl groups, and $R_1$, $R_2$, $R_3$, $R_4$, $R_5$ and $R_6$ are as defined for formula (I),
can also be obtained from a compound of formula (VIII):

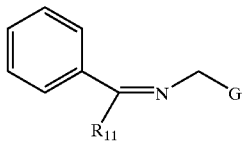
(VIII)

wherein $R_{11}$ represents a hydrogen atom or a phenyl group, and G represents CN or a linear or branched ($C_1$–$C_6$) alkoxycarbonyl group,
which is reacted with a compound of formula (VIa), a particular case of the compounds of formula (VI):

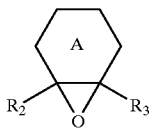
(VIa)

wherein

$R_2$ and $R_3$ are as defined hereinbefore,
to yield a compound of formula (IX) of the relative configuration trans:

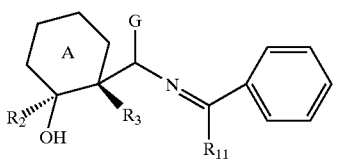
(IX)

wherein

G, $R_2$, $R_3$ and $R_{11}$ are as defined hereinbefore,
which compound of formula (IX):
when it is desired to obtain a compound of the relative configuration trans, is hydrolysed under acid conditions to yield, after optional acylation of the amino function, a compound of formula (Xt) in which the ring junction is trans:

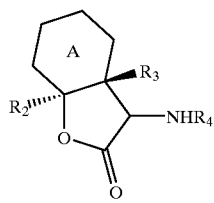
(Xt)

wherein

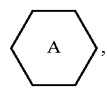

$R_2$, $R_3$ and $R_4$ are as defined hereinbefore,
which is reacted with a compound of formula (II) to yield, after optional acylation of the hydroxy function, a compound of formula (Id) of the relative configuration trans, a particular case of the compounds of formula (Ic):

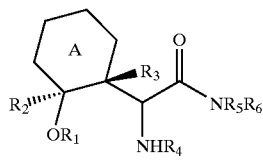
(Id)

wherein

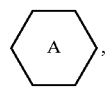

$R_1$, $R_2$, $R_3$, $R_4$, $R_5$ and $R_6$ are as defined hereinbefore,
or, when it is desired to obtain a compound of the relative configuration cis, is subjected to a Mitsunobu reaction to yield, after optional acylation of the amino function, a compound of formula (Xc) in which the ring junction is cis:

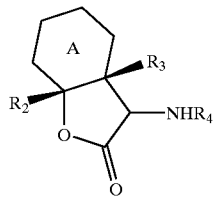
(Xc)

wherein

$R_2$, $R_3$ and $R_4$ are as defined hereinbefore,
which is reacted with a compound of formula (II) to yield, after optional acylation of the hydroxy function, a compound of formula (Ie) of the relative configuration cis, a particular case of the compounds of formula (Ic):

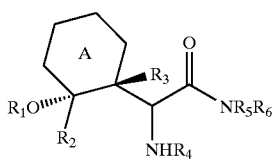
(Ie)

wherein

, $R_1$, $R_2$, $R_3$, $R_4$, $R_5$ and $R_6$ are as defined hereinbefore,
which compounds of formulae (Id) and (Ie) are separated, if desired, into their stereoisomers by conventional separation techniques, are purified, if necessary, by conventional methods of purification, and are converted, if desired, into addition salts with a phamaceutically acceptable acid.

The compounds of formula (If) of the relative configuration cis, a particular case of the compounds of formula (I):

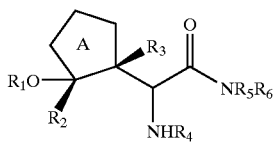
(If)

wherein

represents a saturated carbon ring having 5 chain members optionally substituted by one or more groups selected from linear and branched ($C_1$–$C_6$)alkyl groups, and $R_1$, $R_2$, $R_3$, $R_4$, $R_5$ and $R_6$ are as defined for formula (I),
can also be obtained from a compound of formula (VIII), which is reacted with a compound of formula (VIb), a particular case of the compounds of formula (VI):

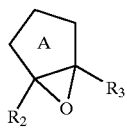
(VIb)

wherein

, $R_2$ and $R_3$ are as defined hereinbefore,
to yield a compound of formula (XI) of the relative configuration trans:

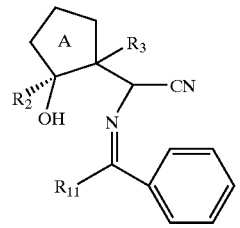
(XI)

wherein

, $R_2$, $R_3$ and $R_{11}$ are as defined hereinbefore, which is hydrolysed under acid conditions to yield, after optional acylation of the amino function, a compound of formula (XII) in which the ring junction is cis:

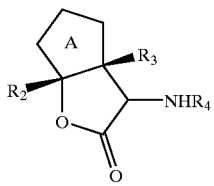
(XII)

wherein

, $R_2$, $R_3$ and $R_4$ are as defined hereinbefore, which is reacted with a compound of formula (II) to yield, after optional acylation of the hydroxy function, a compound of formula (If), which is separated, if desired, into its stereoisomers by conventional separation techniques, is purified, if necessary, by conventional methods of purification and is converted, if desired, into addition salts with a pharmaceutically acceptable acid.

The compounds of formula (Ig) of the relative configuration trans, a particular case of the compounds of formula (I):

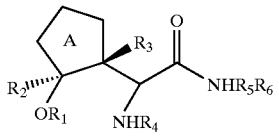
(Ig)

can also be obtained from a compound of formula (XIII):

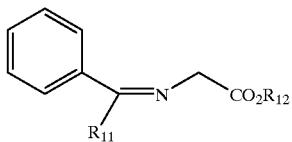
(XIII)

wherein $R_{11}$ is as defined hereinbefore, and $R_{12}$ represents a linear or branched ($C_1$–$C_6$)alkyl group,
which is reacted with a compound of formula (VIb) to yield a compound of formula (XIV) of the relative configuration trans:

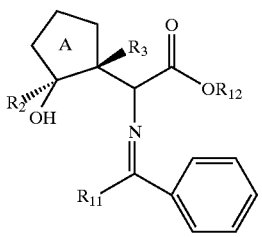
(XIV)

wherein

, $R_2$, $R_3$, $R_{11}$ and $R_{12}$ are as defined hereinbefore,
which is hydrolysed under mild acid conditions to yield, after acylation or protection of the amino function, a compound of formula (XV) of the relative configuration trans:

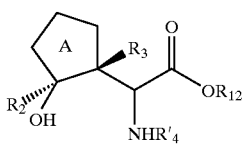
(XV)

wherein

, $R_2$, $R_3$ and $R_{12}$ are as defined hereinbefore, and $R'_4$ represents either a linear or branched ($C_1$–$C_6$)alkyl group or an amino function-protecting group,
which compound of formula (XV) is reacted, under peptide coupling conditions, with a compound of formula (II) to yield, after optional acylation of the hydroxy function and optional deprotection of the amino function, a compound of formula (Ig), which is separated, if desired, into its stereoisomers by conventional separation techniques, is purified, if necessary, by conventional methods of purification and is converted, if desired, into addition salts with a pharmaceutically acceptable acid.

In addition to the fact that they are new, the compounds of the present invention have valuable pharmacological properties. They have blood glucose-lowering properties, rendering them beneficial in the treatment of glucose intolerance and disorders associated with hyperglycaemia, such as type II diabetes or obesity.

The invention extends also to pharmaceutical compositions comprising as active intredient at least one compound of formula (I) with one or more appropriate, inert, non-toxic excipients. Amongst the pharmaceutical compositions according to the invention there may be mentioned more especially those which are suitable for oral, parenteral (intravenous, intramuscular or subcutaneous) or nasal administration, tablets or dragees, sublingual tablets, gelatin capsules, lozenges, suppositories, creams, ointments, dermal gels, injectable preparations, drinkable suspensions, etc.

The useful dosage is adaptable in accordance with the nature and severity of the disorder, the administration route and also the age and weight of the patient and any associated treatments. The dosage ranges from 0.5 mg to 2 g per 24 hours in one or more administrations.

The Examples which follow illustrate the invention but do not limit it in any way.

The starting materials used are known products or products prepared according to known preparation procedures.

The structures of the compounds described in the Examples were determined according to customary spectrometric techniques (infra-red, NMR, mass spectrometry).

A (1R*,2R*,1'S*) compound is to be understood as a racemic mixture of the 2 enantiomers having the absolute configurations (1R,2R,1'S) and (1S,2S,1'R).

A (1R*,2R*,1'RS) compound is to be understood as a mixture of the 4 stereoisomers having the absolute configurations (1R,2R,1'R), (1R,2R,1'S), (1S,2S,1'R) and (1S,2S,1'S).

A compound having a (1α,2β,1'β) or (1β,2α,1'α) configuration is to be understood as a compound selected from the compounds having the absolute configurations (1R,2S,1'S) and (1S,2R,1'R), wherein when the (1α,2β,1'β) compound represents the compound having the (1R,2S,1'S) configuration, then the (1β,2α,1'α) compound represents the other enantiomer.

A fumarate of a compound is to be understood as a 1:1 addition salt of the said compound with fumaric acid (1 mol of fumaric acid per mol of compound). A hemifumarate of a compound is to be understood as a 1:0.5 addition salt of the said compound with fumaric acid (0.5 mol of fumaric acid per mol of compound).

EXAMPLE 1

(1R*,2S*,1'S*)-2-[1'-Amino-2'-oxo-2'-(1-pyrrolidinyl)ethyl]-cyclohexanol Fumarate Step A: (2RS,1'R*,2'S*)-2-[(Diphenylmethylene)amino]2-(2'-hydroxycyclohexyl)-acetonitrile 10 mmol of a 2.5M n-butyllithium solution are added at −30/−40° C. to 10 mmol of diisopropylamine dissolved in tetrahydrofuran and then, after stirring for 15 minutes at that temperature, the reaction mixture is cooled to −70° C. and 10 mmol of [(diphenyl-methylene)amino]acetonitrile dissolved in tetrahydrofuran are added. After stirring for 4 hours at −70° C., 10 mmol of cyclohexene oxide in tetrahydrofuran are added, followed by 10 mmol of boron trifluoride etherate. The reaction mixture is stirred for a further hour at −70° C., and is then brought to +10° C. before being hydrolysed.

Step B: (3R*,3aR*,7aS*)-3-Aminohexahydro-1-benzofuran-2(3H)-one 160 ml of 4M hydrochloric acid are added to the crude mixture obtained in the above Step. The reaction mixture is then stirred for 3 days, and subsequently decanted. The aqueous phase is washed with diethyl ether, then 25 ml of concentrated hydrochloric acid are added and the reaction mixture is heated at 60° C. for 5 days. After returning to ambient temperature, the solvents are evaporated off. Water is added to the residue obtained, and then potassium carbonate in an amount sufficient to obtain a pH of 9–10. After extraction with dichloromethane, the combined organic phases are dried, filtered, and then evaporated. The residue obtained is purified by chromatography on silica (eluant: dichloromethane/methanol 95/5), and then the diastereoisomers are separated by preparative HPLC. The expected product is the first of the diastereoisomers separated in that way.

Step C: (1R*,2S*,1'S*)-2-[1'-Amino-2'-oxo-2'-(1-pyrrolidinyl)ethyl]cyclohexanol 20 mmol of pyrrolidine are added to 10 mmol of the compound obtained in the above Step dissolved in toluene. After stirring for 24 hours at ambient temperature, the solvent is evaporated off. The residue obtained is purified by chromatography on silica (eluant: dichloromethane/methanol/ammonia 90/10/1) to yield the expected product in the form of a racemic mixture.

Step D: (1R*,2S*,1'S*)-2-[1'-Amino-2'-oxo-2'(1-pyrrolidinyl)ethyl]cyclohexanol Fumarate:

The compound obtained in the above Step is converted into its fumarate by reaction with an ethanolic solution of fumaric acid, filtration, and then drying, to yield the expected product.

EXAMPLE 2A (1α,2β,1'β)-2-[1'-Amino-2'-oxo-2'-(1-pyrrolidinyl) ethyl]cyclohexanol Fumarate The racemic mixture obtained in Step C of Example 1 is separated by preparative chiral HPLC chromatography (column: Chiralpack AS, eluant: n-heptane/isopropanol/diethylamine). The first of the enantiomers obtained is converted into its fumarate by reaction with an ethanolic solution of fumaric acid, filtration, and then drying, to yield the expected product in the form of a white solid.

Melting point: 190–192° C.
Index of rotation: $\alpha_D = -20.23°$ (water, c=1, $\lambda$=365 nm)
Elemental microanalysis:

|  | C % | H % | N % |
| --- | --- | --- | --- |
| calculated | 56.13 | 7.65 | 8.18 |
| found | 56.13 | 7.74 | 8.05 |

EXAMPLE 2B (1β,2α,1'α)-2-[1'-Amino-2'-oxo-2'-(1-pyrrolidinyl) ethyl]cyclohexanol Fumarate The expected product is obtained by conversion of the second of the enantiomers obtained in Example 2A into its fumarate.

Melting point: 190° C.
Elemental microanalysis:

|  | C % | H % | N % |
| --- | --- | --- | --- |
| calculated | 56.13 | 7.65 | 8.18 |
| found | 56.08 | 7.71 | 8.06 |

EXAMPLE 3

(1R*,2R*,1'R*)-2-[1'-Amino-2'-oxo-2'-(1-pyrrolidinyl)ethyl]-cyclopentanol Fumarate Step A: (1R*,2R*,1'RS)-2-[1'-Amino-2'-oxo-2'-(1-pyrrolidinyl)ethyl]cyclopentanol The expected product is obtained in accordance with the procedure described in Steps A to C of Example 1, with the replacement of cyclohexene oxide with cyclopentene oxide.

Step B: (1R*,2R*,1'R*)-2-[1'-Amino-2'-oxo-2'-(1-pyrrolidinyl)ethyl]cyclopentanol Fumarate The compound obtained in the above Step is purified by chromatography on silica (eluant: dichloromethane/methanol/ammonia 90/10/1). The first of the diastereoisomers obtained in the order of elution is then converted into its fumarate to yield the expected product.

Melting point: 175° C.
Elemental microanalysis:

|  | C % | H % | N % |
| --- | --- | --- | --- |
| calculated | 54.87 | 7.37 | 8.53 |
| found | 55.14 | 7.56 | 8.48 |

EXAMPLE 4

(1R*,2R*,1'S*)-2-[1'-Amino-2'-oxo2'-(1-pyrrolidinyl)ethyl]-cyclopentanol Hemifumarate The expected product is obtained by conversion of the second of the diastereoisomers obtained in Step B of Example 3 into its hemifumarate.

Melting point: 210° C.
Elemental microanalysis:

|  | C % | H % | N % |
| --- | --- | --- | --- |
| calculated | 57.76 | 8.20 | 10.36 |
| found | 57.89 | 8.25 | 10.29 |

EXAMPLE 5

(1α,2α,1'α)-2-[1'-Amino-2'-oxo-2'-(1-pyrrolidinyl) ethyl]-cyclopentanol Fumarate The racemic mixture of Example 3 is separated by preparative chiral HPLC chromatography. The first of the enantiomers obtained is converted into its fumarate by reaction with an ethanolic solution of fumaric acid, filtration, and then drying, to yield the expected product in the form of a white solid.

EXAMPLE 6

(1β,2β,1'β)-2-[1'-Amino-2'-oxo-2'-(1-pyrrolidinyl) ethyl]cyclopentanol Fumarate

The expected product is obtained by conversion of the second of the enantiomers obtained in Example 5 into its fumarate.

EXAMPLE 7

(1R*,2S*,1'R*)-2-[1'-Amino-2'-oxo-2'-(1-pyrrolidinyl)ethyl]-cyclopentanol Hemifumarate Step A: Ethyl [(diphenylmethylene)amino]-(2-hydroxycyclopentyl)-acetate The expected product is obtained in accordance with the procedure described in Step A of Example 1, starting from ethyl N-diphenylmethylene glycinate and cyclopentene oxide.

Step B: Ethyl (1R*,2S*,1'RS)-amino-(2-hydroxycyclopentyl)-acetate 24 mmol of a 1M hydrochloric acid solution are added to 10 mmol of the compound obtained in the above Step dissolved in ether. The reaction mixture is then stirred for 30 minutes at ambient temperature and subsequently decanted. The aqueous phase is then washed with ether, and its pH is subsequently adjusted to from 7 to 8 by the addition of potassium carbonate. After extraction with dichloromethane, the organic phase is dried and then filtered, and the solvent is evaporated off to yield the expected product.

Step C: Ethyl (1R*,2S*,1'R*)-amino-(2-hydroxycyclopentyl)-acetate

The residue obtained in the above Step is chromatographed on silica (eluant: dichloromethane/methanol 90/10). The expected product is the first of the 2 diastereoisomers separated in that way.

Step D: Ethyl (1R*,2S*,1'R*)-[(benzyloxycarbonyl)amino]-(2-hydroxycyclopentyl)-acetate To 10 mmol of the compound obtained in the above Step dissolved in ethyl acetate there are added a saturated sodium hydrogen carbonate solution and then, dropwise, 10 mmol of benzyl chloroformate. After stirring for 2 hours at ambient temperature, the reaction mixture is decanted, the aqueous phase is extracted with ethyl acetate, and then the combined organic phases are washed, dried, filtered, and subsequently evaporated. The residue obtained is purified by chromatography on silica (eluant: dichloromethane/methanol 95/5) to yield the expected product.

Step E: (1R*,2S*,1'R*)-[(Benzyloxycarbonyl)amino]-(2-hydroxycyclopentyl)acetic Acid 10 mmol of a 1M sodium hydroxide solution are added to 10 mmol of the compound obtained in the above Step dissolved in ethanol. The reaction mixture is then heated at reflux for 1 hour, and subsequently the ethanol is evaporated off, and water and then 10 mmol of citric acid are added to the residue obtained. The aqueous phase is subsequently extracted with dichloromethane and then dried, filtered and concentrated to yield the expected product.

Step F: (1R*,2S*,1'R*)-2-[1'-[(Benzyloxycarbonyl)amino]-2'-oxo-2'-(1-pyrrolidinyl)-ethyl]cyclopentanol To 10 mmol of the compound obtained in the above Step dissolved in tetrahydrofuran there are added 12 mmol of pyrrolidine and 20 mmol of diisopropylethylamine, and then a mixture of 12 mmol of 1-hydroxybenzotriazole and 12 mmol of 2-(1H-benzotriazol-1-yl)-1,1,3,3-tetramethyluronium tetrafluoroborate. The reaction mixture is then stirred at ambient temperature for one night, ethyl acetate is subsequently added, and the organic phase is washed, dried, filtered and then concentrated to yield the expected product.

Step G: (1R*,2S*,1'R*)-2-[1'-Amino-2'-oxo-2'-(1-pyrrolidinyl)ethyl]cyclopentanol Hemifumarate 1.7 g of 10% Pd/C are added to 10 mmol of the compound obtained in the above Step dissolved in ethanol, and the mixture is then hydrogenated at 90 mbars for 16 hours. After removal of the catalyst by filtration through Celite and washing with ethanol, the filtrate is concentrated and the residue obtained is then purified by chromatography on silica (eluant: dichloromethane/methanol/NH$_4$OH 90/10/1). The product so obtained is converted into its fumarate by the addition of a solution of fumaric acid in isopropanol, followed by crystallisation.

Melting point: 193° C.

Elemental microanalysis:

|  | C % | H % | N % |
| --- | --- | --- | --- |
| calculated | 57.76 | 8.20 | 10.36 |
| found | 57.38 | 8.07 | 10.23 |

EXAMPLE 8

(1R*,2S*,1'S*)-2-[1'-Amino-2'-oxo-2'-(1-pyrrolidinyl)ethyl]-cyclopentanol Fumarate The expected product is obtained in accordance with the procedure described in Steps D to G of Example 7, starting from the second of the diastereoisomers separated in Step C of Example 7. The product so obtained is converted into its fumarate by the addition of a solution of fumaric acid in isopropanol, followed by crystallisation.

Melting point: 170° C.

Elemental microanalysis:

|  | C % | H % | N % |
| --- | --- | --- | --- |
| calculated | 54.87 | 7.37 | 8.53 |
| found | 54.44 | 7.28 | 8.66 |

EXAMPLE 9A (1α,2β,1'α)-2-[1'-Amino-2'-oxo-2'-(1-pyrrolidinyl)ethyl]-cyclopentanol Hemifumarate The racemic mixture obtained in Step G of Example 7 is separated by preparative chiral HPLC chromatography on a Chiralpack AD column (eluant: n-heptane/ethanol/diethylamine 75/25/1). The first of the enantiomers so obtained is converted into its hemifumarate by the addition of a solution of fumaric acid in isopropanol, followed by crystallisation.

Elemental microanalysis:

|  | C % | H % | N % |
| --- | --- | --- | --- |
| calculated | 57.76 | 8.20 | 10.36 |
| found | 58.08 | 8.13 | 10.11 |

EXAMPLE 9B (1α,2β,1'α)-2-[1'-Amino2'-oxo-2'-(1-pyrrolidinyl)ethyl]-cyclopentanol Fumarate The first of the enantiomers obtained in Example 9A is converted into its fumarate by the addition of a solution of fumaric acid in isopropanol, followed by crystallisation.

Melting point: 162° C.

Elemental microanalysis:

|  | C % | H % | N % |
|---|---|---|---|
| calculated | 54.87 | 7.37 | 8.53 |
| found | 54.58 | 7.38 | 8.49 |

EXAMPLE 10

(1β,2α,1'β)2-[1'-Amino-2'-oxo-2'-(1-pyrrolidinyl) ethyl]-cyclopentanol Fumarate

The second of the enantiomers separated in Example 9A is converted into its fumarate by the addition of a solution of fumaric acid in isopropanol, followed by crystallisation.

Elemental microanalysis:

|  | C % | H % | N % |
|---|---|---|---|
| calculated | 54.87 | 7.37 | 8.53 |
| found | 54.97 | 7.43 | 8.41 |

EXAMPLE 11

(1α,2β,1'β)-2-[1'-Amino-2'-oxo-2'-(1-pyrrolidinyl) ethyl]-cyclopentanol Hemifumarate The racemic mixture of Example 8 is separated by preparative chiral HPLC chromatography. The first of the enantiomers so obtained is converted into its fumarate by the addition of a solution of fumaric acid in isopropanol, followed by crystallisation.

Melting point: 187° C.

Index of rotation): $\alpha_D = -22.73°$ (water, c=1, λ=589 nm)

Elemental microanalysis:

|  | C % | H % | N % |
|---|---|---|---|
| calculated | 57.76 | 8.20 | 10.36 |
| found | 57.47 | 8.21 | 10.15 |

EXAMPLE 12

(1β,2α,1'α)-2-[1'-Amino-2'-oxo-2'-(1-pyrrolidinylethyl]-cyclopentanol Hemifumarate The second of the enantiomers separated in Example 11 is converted into its hemifumarate by the addition of a solution of fumaric acid in isopropanol, followed by crystallisation.

Melting point: 185° C.

Index of rotation: $\alpha_D = +22.95°$ (water, c=1, λ=589 nm)

Elemental microanalysis:

|  | C % | H % | N % |
|---|---|---|---|
| calculated | 57.76 | 8.20 | 10.36 |
| found | 57.47 | 8.24 | 10.15 |

EXAMPLE 13

(1α,2α1'β)-2-[1'-Amino-2'-oxo-2'-(1-pyrrolidinyl) ethyl]-cyclopentanol Hemifumarate The racemic mixture of Example 4 is separated by preparative chiral HPLC chromatography on a Chiralpack AD column (eluant: n-heptane/ethanol/diethylamine 80/20/1). The first of the enantiomers so obtained is converted into its hemifumarate by the addition of a solution of fumaric acid in isopropanol, followed by crystallisation.

Melting point: 180° C.

Index of rotation: $\alpha_D = +18.95°$ (water, c=1, λ=589 nm)

Elemental microanalysis:

|  | C % | H % | N % |
|---|---|---|---|
| calculated | 57.76 | 8.20 | 10.36 |
| found | 56.63 | 7.83 | 9.50 |

EXAMPLE 14

(1R*,2S*,1'R*)-2-[1'-Amino-2'-oxo-2'-(1-morpholinyl)ethyl]-cyclopentanol Hemifumarate The expected product is obtained in accordance with the procedure described in Example 7, with the replacement of pyrrolidine with morpholine in Step F.

Melting point: 192° C.

Elemental microanalysis:

|  | C % | H % | N % |
|---|---|---|---|
| calculated | 52.32 | 7.02 | 8.13 |
| found | 53.49 | 7.49 | 9.41 |

EXAMPLE 15

(1R*,2S*,1'S*)-2-[1'-Amino-2'-oxo-2'-(1-morpholinyl)ethyl]-cyclopentanol Hemifumarate The expected product is obtained in accordance with the procedure described in Steps D to G of Example 7, starting from morpholine and the second of the diastereoisomers separated in Step C of Example 7.

Elemental microanalysis:

|  | C % | H % | N % |
|---|---|---|---|
| calculated | 52.32 | 7.02 | 8.13 |
| found | 52.83 | 7.11 | 8.77 |

EXAMPLE 16

(1R*,2S*,1'R*)-2-[1'-Amino-2'-oxo-2'-(1-azetidinyl) ethyl]-cyclopentanol Hemifumarate The expected product is obtained in accordance with the procedure described in Example 7, with the replacement of pyrrolidine with azetidine in Step F.

Melting point: 208° C.
Elemental microanalysis:

|  | C % | H % | N % |
|---|---|---|---|
| calculated | 56.24 | 7.87 | 10.93 |
| found | 56.25 | 7.84 | 10.66 |

EXAMPLE 17

(1R*,2S*,1'S*)-2-[1'-Amino-2'-oxo-2'-(1-azetidinyl)ethyl]-cyclopentanol Hemifumarate The expected product is obtained in accordance with the procedure described in Steps D to G of Example 7, starting from azetidine and the second of the diastereoisomers separated in Step C of Example 7.

Melting point: 206° C.
Elemental microanalysis:

|  | C % | H % | N % |
|---|---|---|---|
| calculated | 56.24 | 7.87 | 10.93 |
| found | 55.99 | 7.82 | 10.73 |

EXAMPLE 18

(1R*,2S*,1'R*)-2-[1'-Amino-2'-oxo-2'-(1-piperidyl)ethyl]-cyclopentanol Hemifumarate The expected product is obtained in accordance with the procedure described in Example 7, with the replacement of pyrrolidine with piperidine in Step F.

Melting point: 188° C.
Elemental microanalysis:

|  | C % | H % | N % |
|---|---|---|---|
| calculated | 59.14 | 8.51 | 9.85 |
| found | 58.82 | 8.45 | 9.65 |

EXAMPLE 19

(1R*,2S*,1'S*)-2-[1'-Amino-2'-oxo-2'-(1-piperidyl)ethyl]-cyclopentanol Hemifumarate The expected product is obtained in accordance with the procedure described in Steps D to G of Example 7, starting from piperidine and the second of the diastereoisomers separated in Step C of Example 7.

Melting point: 130° C.
Elemental microanalysis:

|  | C % | H % | N % |
|---|---|---|---|
| calculated | 59.14 | 8.51 | 9.85 |
| found | 59.02 | 8.54 | 9.68 |

EXAMPLE 20

(1R*,2S*,1'R*)-2-[1'-Amino-2'-oxo-2'-(2-azabicyclo[3.3.0]octan-2-yl)ethyl]cyclopentanol Hemifumarate The expected product is obtained in accordance with the procedure described in Example 7, with the replacement of pyrrolidine with 2-azabicyclo[3.3.0]octane in Step F.

Melting point: 194° C.

Elemental microanalysis:

|  | C % | H % | N % |
|---|---|---|---|
| calculated | 61.91 | 8.44 | 9.03 |
| found | 61.65 | 8.36 | 8.90 |

EXAMPLE 21

(1R*,2S*,1'S*)-2-[1'-Amino-2'-oxo-2'-(2-azabicyclo[3.3.0]octan-2-yl)ethyl]cyclopentanol Hemifumarate The expected product is obtained in accordance with the procedure described in Steps D to G of Example 7, starting from 2-azabicyclo[3.3.0]octane and the second of the diastereoisomers separated in Step C of Example 7.

Melting point: 185° C.

Elemental microanalysis:

|  | C % | H % | N % |
|---|---|---|---|
| calculated | 61.91 | 8.44 | 9.03 |
| found | 61.52 | 8.33 | 8.87 |

EXAMPLE 22

(1R*,2S*,1'R*)-2-[1'-Amino-2'-oxo-2'-(1,3-thiazolidin-3-yl)ethyl]-cyclopentanol Hemifumarate Step A: Ethyl (1R*,2S*,1'R*)-[(tert-butyloxycarbonyl)amino]-(2-hydroxycyclopentyl)-acetate A solution of 1N sodium hydroxide (11 mmol) and di-tert-butyl dicarbonate (11 mmol) is added to 10 mmol of the compound described in Step C of Example 7 dissolved in tert-butanol. After stirring for 1 hour, the solvents are removed by evaporation, the residue is taken up in ethyl acetate, and the organic phase is washed, dried and evaporated to yield the expected product.

Step B: (1R*,2S*,1'R*)-2-[1'-{(Tert-butyloxycarbonyl)-amino}-2'-oxo-2'-(1,3-thiazolidin-3yl)-ethyl]-cyclopentanol The expected product is obtained in accordance with the procedure described in Steps E and F of Example 7, with the replacement of pyrrolidine with 1,3-thiazolidine in Step F.

Step C. (1R*,2S*,1'R*)-2-[1'-Amino-2'-oxo-2'-(1,3-thiazolidin-3-yl)-ethyl]-cyclopentanol The product obtained in the preceding Step is deprotected by magnesium perchlorate, in acetonitrile at reflux, according to the procedure described in Chem. Comm. 1999, p. 1809–1810, to yield the expected product.

Step D: (1R*,2S*,1'R*)-2-[1'-Amino-2'-oxo-2'-(1,3-thiazolidin-3-yl)ethyl]-cyclopentanol Hemifumarate The product obtained in the preceding Step is converted into its hemifumarate by the addition of a solution of fumaric acid in isopropanol, followed by crystallisation.

Melting point: 207° C.
Elemental microanalysis:

|  | C % | H % | N % | S % |
|---|---|---|---|---|
| calculated | 49.98 | 6.99 | 9.71 | 11.12 |
| found | 49.68 | 7.06 | 9.51 | 11.33 |

EXAMPLE 23

(1R*,2S*,1'S*)-2-[1'-Amino-2'-oxo-2'-(1,3-thiazolidin-3-yl)ethyl]-cyclopentanol Fumarate The expected product is obtained in accordance with the procedure described in Example 22, starting from 1,3-thiazolidine and the second of the diastereoisomers separated in Step C of Example 7.

Melting point: 190° C.
Elemental microanalysis:

|  | C % | H % | N % | S % |
|---|---|---|---|---|
| calculated | 48.54 | 6.40 | 8.09 | 9.26 |
| found | 48.86 | 6.49 | 7.85 | 9.20 |

EXAMPLE 24

(1R*,2S*,1'S*)-2-[1'-Amino-2'-oxo-2'-(1-pyrrolidinyl)ethyl]-cyclohexanol Fumarate Step A: (1R*,2S*,1'S*)-2-[1'-Amino-2'-oxo-2'-(1-pyrrolidinyl)ethyl]cyclohexanol The expected product is obtained in accordance with the procedure described in Step C of Example 1, starting from the second of the diastereoisomers obtained in Step B of Example 1.

Step B: (1R*,2S*,1'S*)-2-[1'-Amino-2'-oxo-2'-(1-pyrrolidinyl)ethyl]cyclohexanol Fumarate The expected product is obtained in accordance with the procedure described in Step D of Example 1, starting from the compound obtained in the above Step.

Melting point: 174° C.
Elemental microanalysis:

|  | C % | H % | N % |
|---|---|---|---|
| calculated | 56.13 | 7.65 | 8.18 |
| found | 55.86 | 7.60 | 8.16 |

EXAMPLE 25

(1α,2β,1'β)-2-[1'-Amino-2'-oxo-2'-(1-pyrrolidinyl)ethyl]-cyclohexanol Fumarate

The racemic mixture obtained in Step A of Example 24 is separated by preparative chiral HPLC chromatography (eluant: n-heptane/ethanol/diethylamine 90/10/1). The first of the enantiomers obtained is converted into its fumarate by reaction with an ethanolic solution of fumaric acid, filtration, and then drying, to yield the expected product in the form of a white solid.

Melting point: 165° C.
Elemental microanalysis:

|  | C % | H % | N % |
|---|---|---|---|
| calculated | 56.13 | 7.65 | 8.18 |
| found | 56.21 | 7.50 | 8.27 |

Index of rotation: :$\alpha_D$=+33.17° (water, c=1, $\lambda$=589 nm).

EXAMPLE 26

(1β,2α,1'α)-2-[1'-Amino-2'-oxo-2'-(1-pyrrolidinyl)ethyl]-cyclohexanol Fumarate

The second of the enantiomers obtained in Example 25 is converted into its fumarate by reaction with an ethanolic solution of fumaric acid, filtration, and then drying, to yield the expected product in the form of a white solid.

Elemental microanalysis:

|  | C % | H % | N % |
|---|---|---|---|
| calculated | 56.13 | 7.65 | 8.18 |
| found | 55.88 | 7.65 | 8.19 |

Index of rotation: :$\alpha_D$=−33.27° (water, c=1, $\lambda$=589 nm).

EXAMPLE 27

(1R*,2R*,1'S*)-2-[1'-Amino-2'-oxo-2'-(1-pyrrolidinyl)ethyl]-cyclohexanol Fumarate Step A: (3S*,3aR*,7aR*)-3-Aminohexahydro-1-benzofuran-2(3H)-one The compound obtained in Step A of Example 1 is subjected to a Mitsunobu reaction in accordance with the procedure described in Synthesis 1981, pp. 1 to 28. The product so obtained is purified by chromatography on silica, and the diastereoisomers are then separated by preparative HPLC. The expected product is the first of the diastereoisomers separated in that way.

Step C: (1R*,2R*,1'S*)-2-[1'-Amino-2'-oxo-2'-(1-pyrrolidinyl)ethyl]cyclohexanol Fumarate The expected product is obtained in accordance with the procedure described in Steps C and D of Example 1, starting from the compound obtained in the above Step.

Melting point: 198° C.
Elemental microanalysis:

|  | C % | H % | N % |
|---|---|---|---|
| calculated | 56.13 | 7.65 | 8.18 |
| found | 55.92 | 7.62 | 8.14 |

EXAMPLE 28

(1R*,2R*,1'R*)-2-[1'-Amino-2'-oxo-2'-(1-pyrrolidinyl)ethyl]-cyclohexanol Fumarate The expected product is obtained in accordance with the procedure described in Steps C and D of Example 1, starting from the second of the diastereoisomers separated in Step A of Example 27.

Melting point: 180° C.

Elemental microanalysis:

|  | C % | H % | N % |
|---|---|---|---|
| calculated | 56.13 | 7.65 | 8.18 |
| found | 55.83 | 7.60 | 8.11 |

EXAMPLE 29

(1R*,2S*,1'R*)-2-[1'-Amino-2'-oxo-2'-(2,5-dihydro-1H-pyrrol-1-yl)ethyl]cyclohexanol Fumarate The expected product is obtained in accordance with the procedure described in Steps C and D of Example 1, starting from 2,5-dihydro-1H-pyrrole and the second of the diastereoisomers obtained in Step B of Example 1.

Elemental microanalysis:

|  | C % | H % | N % |
|---|---|---|---|
| calculated | 56.46 | 7.11 | 8.23 |
| found | 56.06 | 6.77 | 8.21 |

EXAMPLE 30

(1R*,2S*,1'R*)-2-[1-Amino-2'-oxo-2'-(1,3-thiazolidin-3-yl)ethyl]-cyclohexanol Fumarate Step A: (1R*,2S*,1'R*)-2-[1'-Amino-2'-oxo-2'-(1,3-thiazolidin-3-yl)ethyl]-cyclohexanol The expected product is obtained in accordance with the procedure described in Step C of Example 1, starting from 1,3-thiazolidine and the second of the diastereoisomers obtained in Step B of Example 1.

Step B: (1R*,2S*,1'R*)-2-[1'-Amino-2-oxo-2'(1,3-thiazolidin-3-yl)ethyl]-cyclohexanol Fumarate The expected product is obtained in accordance with the procedure described in Step D of Example 1, starting from the compound obtained in the above Step.

Melting point: 195° C.

Elemental microanalysis:

|  | C % | H % | N % | S % |
|---|---|---|---|---|
| calculated | 49.99 | 6.71 | 7.77 | 8.90 |
| found | 50.16 | 6.72 | 7.55 | 8.88 |

EXAMPLE 31

(1α,2β,1'α)-2-[1'-Amino-2'-oxo-2'-(1,3-thiazolidin-3-yl)ethyl]-cyclohexanol Fumarate The racemic mixture obtained in Step A of Example 30 is separated by preparative chiral HPLC chromatography (eluant=ethanol/diethylamine 1000/1). The first of the enantiomers obtained is converted into its fumarate by reaction with an ethanolic solution of fumaric acid, filtration, and then drying, to yield the expected product in the form of a white solid.

Melting point: 190° C.

Elemental microanalysis:

|  | C % | H % | N % | S % |
|---|---|---|---|---|
| calculated | 49.99 | 6.71 | 7.77 | 8.90 |
| found | 49.79 | 6.74 | 7.57 | 8.86 |

Index of rotation: :$\alpha_D = -30.11°$ (water, c=1, $\lambda$=589 nm).

EXAMPLE 32

(1β,2α,1'β)-2-[1'-Amino-2'-oxo-2'-(1,3-thiazolidin-3-yl)ethyl]-cyclohexanol Fumarate The second of the enantiomers obtained in Example 31 is converted into its fumarate by reaction with an ethanolic solution of fumaric acid, filtration, and then drying, to yield the expected product in the form of a white solid.

Melting point: 188° C.

Elemental microanalysis:

|  | C % | H % | N % | S % |
|---|---|---|---|---|
| calculated | 49.99 | 6.71 | 7.77 | 8.90 |
| found | 50.21 | 6.81 | 7.67 | 9.14 |

Index of rotation: :$\alpha_D = +32.11°$ (water, c=1, $\lambda$=589 nm).

EXAMPLE 33

(1R*,2S*,1'R*)-2-[1'-Amino-2'-oxo-2'-(1-pyrrolidinyl)ethyl]-cycloheptanol Fumarate Step A: Ethyl (1R*,2S*,1'RS)-amino-(2-hydroxycycloheptyl)-acetate The expected product is obtained in accordance with the procedure described in Steps A and B of Example 7, with the replacement of cyclopentene oxide with cycloheptene oxide in Step A.

Step B: Ethyl (1R*,2S*,1'R*)-amino-(2-hydroxycycloheptyl)-acetate

The residue obtained in the above Step is chromatographed on silica (eluant: dichloromethane/methanol 90/10). The expected product is the first of the 2 diastereoisomers separated in that way.

Step C: (1R*,2S*,1'R*)-2-[1'-Amino-2'-oxo-2'-(1-pyrrolidinyl)ethyl]cycloheptanol Fumarate The expected product is obtained in accordance with the procedure described in Steps D to of Example 7, starting from the compound obtained in the above Step.

Melting point: 178° C.

Elemental microanalysis:

|  | C % | H % | N % |
|---|---|---|---|
| calculated | 57.29 | 7.92 | 7.86 |
| found | 57.03 | 7.93 | 7.86 |

EXAMPLE 34

(1R*,2S*,1'S*)-2-[1'-Amino-2'-oxo-2'-(1,3-thiazolidin-3-yl)ethyl]-cycloheptanol Fumarate The expected product is obtained in accordance with the procedure described in Steps D to G of Example 7, starting from the second of the diastereoisomers separated in Step B of Example 33.

EXAMPLE 35

(1R*,2S*,1'S*)-2-[1'-Amino-2'-oxo-2'-(N,N-diethylamino)ethyl]-cyclopentanol Fumarate The expected product is obtained in accordance with the procedure described in Steps D to G of Example 7, starting from N,N-diethylamine and the second of the diastereoisomers separated in Step C of Example 7.

Melting point: 108° C.

Elemental microanalysis:

|            | C %   | H %  | N %  |
|------------|-------|------|------|
| calculated | 54.53 | 7.93 | 8.48 |
| found      | 54.10 | 7.86 | 8.57 |

EXAMPLE 36

(1α,2β,1'α)-2-[1'-Amino-2'-oxo-2'-(1,3-thiazolidin-3-yl)ethyl]-cyclopentanol Fumarate The racemic mixture obtained in Step C of Example 22 is separated by preparative chiral HPLC chromatography. The first of the enantiomers obtained is converted into its fumarate by reaction with an ethanolic solution of fumaric acid, filtration, and then drying, to yield the expected product.

EXAMPLE 37

(1β,2α,1'β)-2-[1'-Amino-2'-oxo-2'-(1,3-thiazolidin-3-yl)ethyl]-cyclopentanol Fumarate The second of the enantiomers obtained in Example 36 is converted into its fumarate by reaction with an ethanolic solution of fumaric acid, filtration, and then drying, to yield the expected product.

Pharmacological Study of the Compounds of the Invention

EXAMPLE 38

Functional Test of Glucose Overload by the Oral Route

Under a general anaesthetic (sodium pentobarbital), obese male Zucker rats (homozygotes fa/fa), aged from 10 to 12 weeks, are subjected to implantation of a catheter (Silastic) in the right jugular vein 24 hours prior to the functional test of glucose overload by the oral route (OGTT). After fasting for 18 hours, the rats, which have been woken and isolated in individual cages, are given by oesophageal intubation 1 g/kg of a 40% solution of D(+)-glucose in water. Administration of the products being tested (25, 10, 5 and 1 mg/kg) is carried out at the same time as the glucose or beforehand (−10, −20 min . . . ). Blood samples are taken by way of the venous catheter at times (−20, −10) 0, 10, 20, 40 and 60 minutes after administering the glucose overload, making it possible to follow the development of insulinaemia activity and glycaemia activity.

The compounds of the invention normalise insulinaemia and glycaemia at doses of from 1 to 25 mg/kg p.o.

EXAMPLE 39

Pharmaceutical Composition

Formulation for the preparation of 1000 tablets each containing a dose of 10 mg

| compound of Example 1 | 10 g |
|---|---|
| hydroxypropyl cellulose | 2 g |
| wheat starch | 10 g |
| lactose | 100 g |
| magnesium stearate | 3 g |
| talc | 3 g |

We claim:

1. A compound selected from those of formula (I):

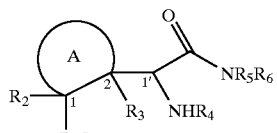

(I)

wherein:

represents a saturated carbon ring having from 4 to 8 ring members, optionally substituted by one or more linear or branched ($C_1$–$C_6$)alkyl groups, $R_1$ and $R_4$, which may be identical or different, each represents hydrogen or linear or branched ($C_1$–$C_6$)acyl, $R_2$ and $R_3$, which may be identical or different, each represents hydrogen or linear or branched ($C_1$–$C_6$) alkyl, $R_5$ and $R_6$, which may be identical or different, each represents hydrogen or linear or branched ($C_1$–$C_6$) alkyl, or $R_5$ and $R_6$ together, with the nitrogen atom carrying them, form a nitrogen-containing heterocycle optionally substituted by one or more identical or different groups selected from cyano, $CO_2R_7$ (wherein $R_7$ represents hydrogen or linear or branched ($C_1$–$C_6$)alkyl), $COR_7$ (wherein $R_7$ is as defined hereinbefore), nitro, $CONR_{8a}R_{8b}$ (wherein $R_{8a}$ and $R_{8b}$, which may be identical or different, each represents hydrogen or linear or branched ($C_1$–$C_6$)alkyl or $R_{8a}$ and $R_{8b}$ together form a nitrogen-containing heterocycle), $S(O)_nR_9$ (wherein n represents 1, 2 or 3, and $R_9$ represents hydrogen, linear or branched ($C_1$–$C_6$)-alkyl or aryl) and $PO_3R_{10a}R_{10b}$ wherein $R_{10a}$ and $R_{10b}$, which may be identical or different, each represents hydrogen or linear or branched ($C_1$–$C_6$)-alkyl, a stereoisomer thereof, or an addition salt thereof with a pharmaceutically acceptable acid, wherein a nitrogen-containing heterocycle is an optionally bridged, saturated mono- or bi-cyclic group having from 5 to 12 ring members and containing one, two or three hetero atoms, one of those hetero atoms being nitrogen and the additional hetero atom or atoms optionally present being selected from oxygen, nitrogen and sulphur, and an aryl group is a phenyl, biphenyl, naphthyl or tetrahydronaphthyl, each of those groups optionally being substituted by one or more identical or different atoms or groups selected from halogen, linear or branched ($C_1$–$C_6$)alkyl, hydroxy, linear or branched ($C_1$–$C_6$)alkoxy, linear or branched ($C_1$–$C_6$) polyhaloalkyl, nitro and ($C_1$–$C_2$)alkylenedioxy.

2. A compound of claim 1, wherein

represents a carbon ring having 5 or 6 ring members.

3. A compound of claim 1, wherein $R_5$ and $R_6$ together form an optionally substituted nitrogen-containing heterocycle.

4. A compound of claim 3, wherein $R_5$ and $R_6$ together form an optionally substituted pyrrolidine or an optionally substituted thiazolidine.

5. A compound of claim 1, which is (1R,2S,1'S)-2-[1'-amino-2'-oxo-2'-(1-pyrrolidinyl)ethyl]cyclohexanol, its (1S,2R,1'R) enantiomer, or an addition salt thereof with a pharmaceutically acceptable acid.

6. A compound of claim 1, which is (1R*,2R*,1'R*)-2-[1'-amino-2'-oxo-2'-(1-pyrrolidinyl)ethyl]cyclopentanol, or an addition salt thereof with a pharmaceutically acceptable acid, it being understood by (1R*,2R*,1'R*) compound a racemic mixture of the 2 enantiomers having the absolute configurations (1R,2R,1'R) and (1S,2S,1'S).

7. A compound of claim 1, which is (1R,2S,1'R)-2-[1'-amino-2'-oxo-2'-(1-pyrrolidinyl)ethyl]cyclopentanol, its (1S,2R,1'S) enantiomer, or an addition salt thereof with a pharmaceutically aceptable acid.

8. A compound of claim 1, which is (1R,2S,1'S)-2-[1'-amino-2'-oxo-2'-(1-pyrrolidinyl)ethyl]cyclopentanol, its (1S,2R,1'R) enantiomer, or an addition salt thereof with a pharmaceutically acceptable acid.

9. A compound of claim 1, which is (1R,2S,1'R)-2-[1'-amino-2'-oxo-2'-(1-pyrrolidinyl)ethyl]cyclohexanol, its (1S,2R,1'S) enantiomer, or an addition salt thereof with a pharmaceutically acceptable acid.

10. A compound of claim 1, which is (1R,2S,1'R)-2-[1'-amino-2'-oxo-2'-(1,3-thiazolidin-3-yl)ethyl]cyclohexanol, its (1S,2R,1'S) enantiomer, or an addition salt thereof with a pharmaceutically acceptable acid.

11. A method for treating a living animal body afflicted with a condition selected from glucose intolerance and disorders associated with hyperglycaemia, such as type II diabetes or obesity, comprising the step of administering to the living animal body in need thereof an amount of a compound of claim 1 which is effective for alleviation of the condition.

12. A pharmaceutical composition useful for treatment of glucose intolerance or of disorders associated with hyperglycaemia, such as type II diabetes or obesity, comprising an effective amount of a compound of claim 1, together with one or more pharmaceutically acceptable excipients or vehicles.

13. A method for treating a living animal body afflicted with diabetes comprising the step of administering to living animal body in need thereof, an amount of a compound of claim 1 which is effective for alleviation of the condition.

14. A pharmaceutical composition useful for treatment of type II diabetes, comprising an effective amount of a compound of claim 1, together with one or more pharmaceutically acceptable excipients or vehicles.

* * * * *